United States Patent [19]

Takahashi

[11] Patent Number: 5,257,617
[45] Date of Patent: Nov. 2, 1993

[54] SHEATHED ENDOSCOPE AND SHEATH THEREFOR

[75] Inventor: Nagashige Takahashi, Tokyo, Japan

[73] Assignee: Asahi Kogaku Kogyo Kabushiki Kaisha, Tokyo, Japan

[21] Appl. No.: 630,896

[22] Filed: Dec. 20, 1990

[30] Foreign Application Priority Data

Dec. 25, 1989 [JP] Japan ................................. 1-335534
Dec. 25, 1989 [JP] Japan ................................. 1-335535

[51] Int. Cl.$^5$ ............................................. A61B 1/00
[52] U.S. Cl. .......................................................... 128/4
[58] Field of Search ......................................... 128/4, 6

[56] References Cited

U.S. PATENT DOCUMENTS

| | | | |
|---|---|---|---|
| 4,436,087 | 3/1984 | Ouchi | 128/6 |
| 4,646,722 | 3/1987 | Silverstein et al. | 128/4 |
| 4,721,097 | 1/1988 | D'Amelio | 128/4 |
| 4,817,616 | 4/1989 | Goldstein | 128/662.06 |
| 4,869,238 | 9/1989 | Opie et al. | 128/6 |
| 4,878,485 | 11/1989 | Adair | 128/6 |
| 4,942,867 | 7/1990 | Takahashi et al. | 128/4 |
| 4,971,035 | 11/1990 | Ito | 128/6 |
| 4,991,564 | 2/1991 | Takahashi et al. | 128/4 |
| 4,991,565 | 2/1991 | Takashashi et al. | 128/4 |

FOREIGN PATENT DOCUMENTS 61-179128 8/1986 Japan .

*Primary Examiner*—Cary E. O'Connor
*Assistant Examiner*—Cindy A. Cherichetti
*Attorney, Agent, or Firm*—Sandler Greenblum & Bernstein

[57] ABSTRACT

A sheathed endoscope has a flexible elongate insert part and a sheath that is removably fitted over the insert part. The sheathed endoscope comprises a distal end part that is provided at the distal end of the insert part, a distal end cover that is provided at the distal end of the sheath and that is removably fitted over the distal end part, and a lock device that is provided on the distal end cover so as to be engageable with the distal end part. The lock device is disengaged from the distal end part by deforming the distal end cover so that the lock device moves radially outward. A sheath for a sheathed endoscope is provided and is removably fitted over a flexible elongate insert part of the endoscope. The sheath comprises a flexible tubular member that is removably fitted over the insert part, a distal end cover that is connected to the distal end of the tubular member so as to be removably fitted over the distal end of the insert part, the cover being made of a shape-memory synthetic resin material that is restored to a previously memorized shape by heating it to a shape restoration temperature, and a lock device that is provided on the distal end cover.

9 Claims, 7 Drawing Sheets

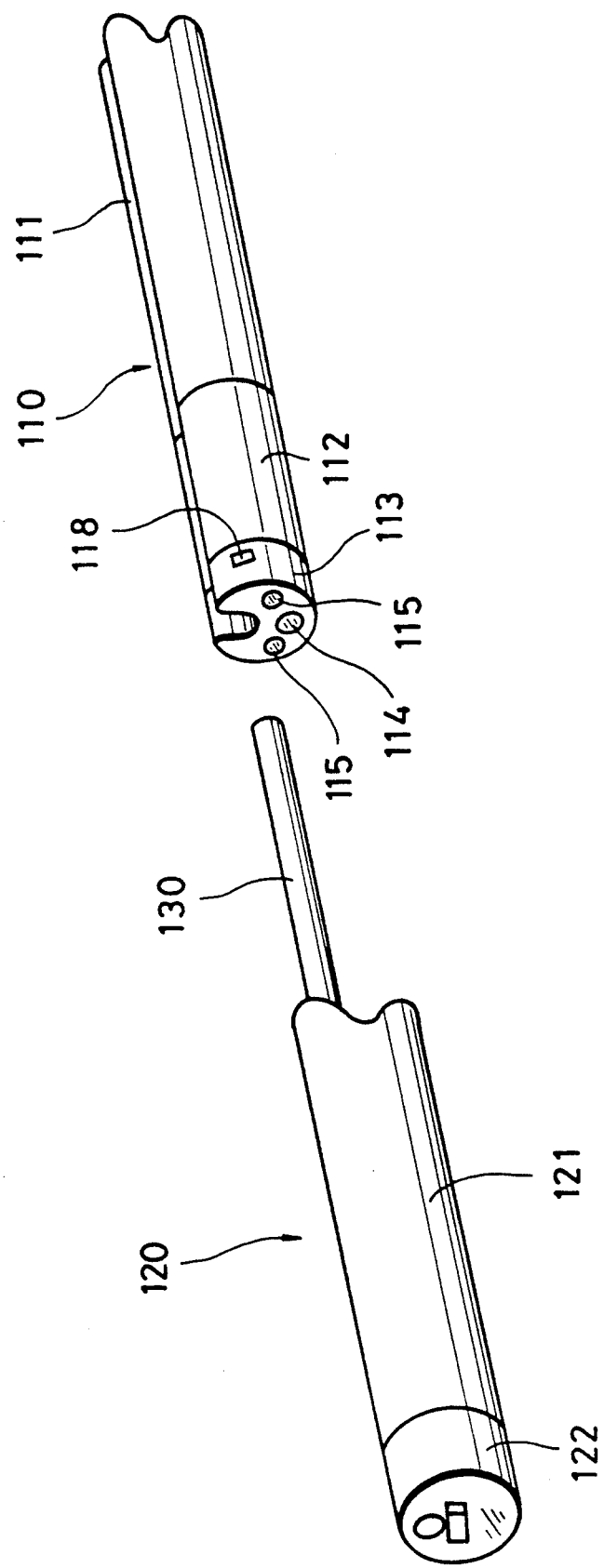

SHEATHED ENDOSCOPE AND SHEATH THEREFOR

BACKGROUND OF THE INVENTION

1. Field of the Invention

The present invention relates to a sheathed endoscope which is designed so that an insert part of the endoscope is covered with a sheath that can be replaced with a new one each time the endoscope has been used in order to prevent the transmission of bacteria and viruses from one patient to another through the endoscope. The present invention also relates to a sheath that is used for the above-described sheathed endoscope.

The present disclosure relates to subject matter contained in Japanese patent application Nos. 1-335534 and 1-335535 (both filed on Dec. 25, 1989) which are expressly incorporated herein by reference in their entirety.

2. Description of the Prior Art

A common sheath that is used for a sheathed endoscope comprises a tube and a transparent distal end cover that is attached to the distal end of the tube, and that is removably fitted over an elongate insert part of the endoscope.

However, when such a sheath is merely fitted over the insert part of an endoscope, a gap may be produced between the distal end cover and the distal end face of the insert part during use. In particular, a sheathed endoscope in which an end portion of a forceps inserting channel for inserting a tool for an endoscopic procedure, for example, a biopsy forceps, is connected to the distal end cover of the sheath involves the problem that the distal end cover may be strongly pushed forward by the forceps inserting channel during use, resulting in a large gap between the distal end cover and the distal end face of the insert part.

Such a sheathed endoscope has a viewing window and illuminating windows, which are provided at the distal end of the insert part, and both an observation light and an illuminating light pass through the transparent distal end cover. Accordingly, if a gap is produced between the distal end cover 251 of the sheath and the distal end face 261 of the insert part of the endoscope, as shown in FIG. 9, part of the illuminating light that is emitted from the illuminating windows 262 enters the viewing window 263 after being reflected at the inner surface of the distal end cover 251. In such a case, an intense flare or ghost may appear in the observation field of view, thus degrading the observation capabilities of the endoscope.

In order to prevent this problem, the distal end cover must be secured to the distal end of the insert part. However, the insert part of the endoscope must be formed as thin as possible with a view to minimizing the pain given to the patient. It is therefore almost impossible to secure the distal end cover to the distal end of the insert part by means, for example, of screws, because of the limited space. In addition, it would be troublesome to untighten and tighten screws for each endoscopic procedure.

SUMMARY OF THE INVENTION

An object of the present invention is to provide a sheathed endoscope which is designed so that the distal end cover of the sheath can be reliably locked to the distal end of the insert part of the endoscope and can be removed therefrom with ease.

Another object of the present invention is to provide a sheath for the above-described sheathed endoscope.

Other objects and advantages of the present invention will become apparent from the following detailed description of illustrated embodiments of the invention.

According to the present invention, there is provided a sheathed endoscope having a flexible elongate insert part and a sheath that is removably fitted over the insert part, comprising: a distal end part that is provided at the distal end of the insert part; a distal end cover that is provided at the distal end of the sheath and that is removably fitted over the distal end part; and a lock device that is provided on the distal end cover so as to be engageable with the distal end part. The lock device is disengaged from the distal end part by deforming the distal end cover so that the lock device moves radially outward.

In addition, there is provided a sheath for a sheathed endoscope that is removably fitted over a flexible elongate insert part of the endoscope, comprising; a flexible tubular member that is removably fitted over the insert part; a distal end cover that is connected to the distal end of the tubular member so as to be removably fitted over the distal end of the insert part, the cover being made of a shape-memory synthetic resin material that is restored to a previously memorized shape by heating it to a shape restoration temperature; and a lock device that is provided on the distal end is engageable with lock device is engageable with the distal end of the insert part at ordinary temperatures and is disengageable therefrom when the distal end cover is restored to the memorized shape.

BRIEF DESCRIPTION OF THE DRAWINGS

The present invention may be more fully understood from the description of preferred embodiments of the invention set forth below, together with the accompanying drawings, in which:

FIG. 4 is a perspective view of a sheath according to a second embodiment of the present invention, which is removed from an insert part of an endoscope;

DESCRIPTION OF THE EMBODIMENTS

Figure 1:
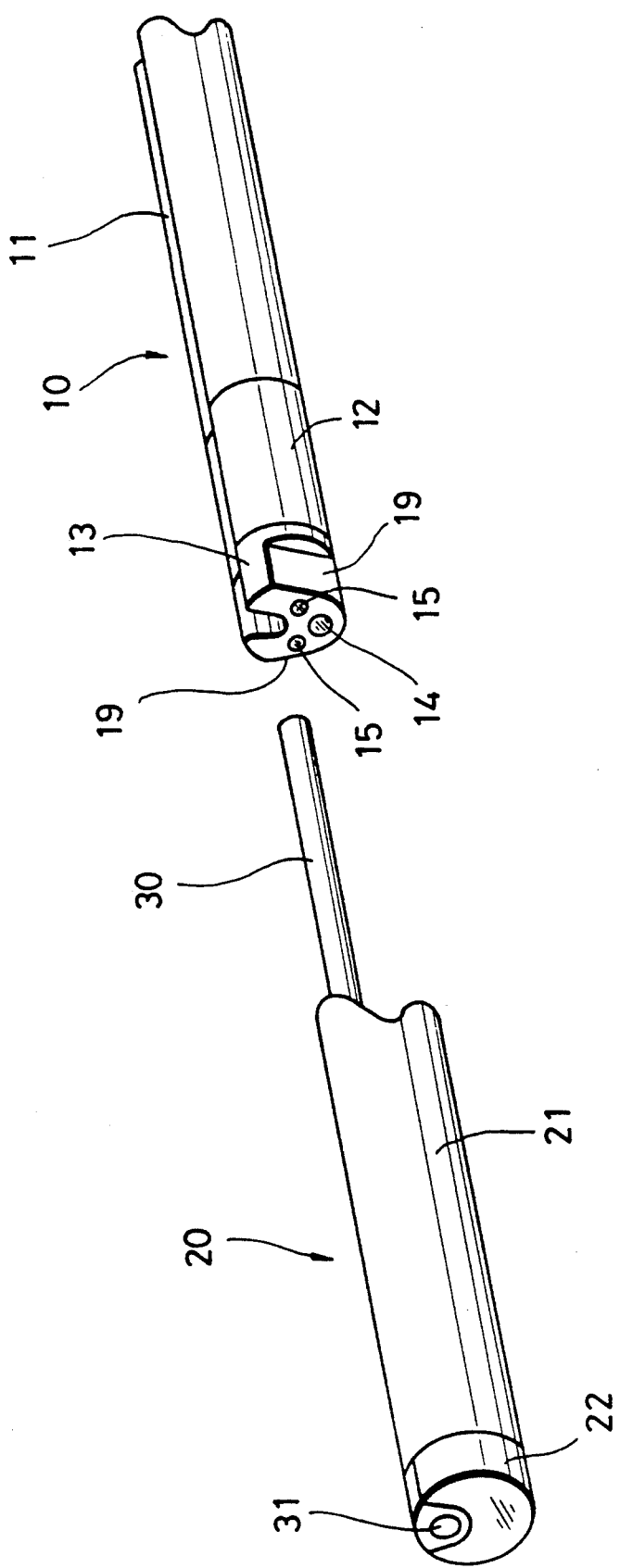
FIG. 1 is a perspective view of a sheath according to a first embodiment of the present invention, which is removed from an insert part of an endoscope.

FIG. 1, which is a perspective view of a first embodiment of the present invention, shows an insert part 10 of an endoscope and the distal end portion of a sheath 20 that is removably fitted over the insert part 10.

The insert part 10 as a whole is formed from an elongate flexible tube. The insert part 10 is formed with a U-shaped groove 11 that extends axially over the entire length thereof in order to avoid interference with a channel tube 30.

A bendable portion 12 that is bendable by remote control is formed at the distal end of the insert part 10. A distal end part 13 that incorporates an objective optical system for observation is connected to the distal end of the bendable portion 12.

The distal end face of the distal end part 13 is provided with a viewing window 14 for the objective optical system and illuminating windows 15 where the emergent end of a light guide fiber bundle is disposed. The windows 14 and 15 slightly project to the same height from the distal end face of the distal end part 13.

The endoscope of this embodiment is an end-viewing endoscope and therefore both of the optical axes of the observation light and the illuminating light are coincident with the axis of the insert part 10.

The distal end part 13 is formed from a cylindrical material. The upper side of the cylindrical material is provided with a U-shaped groove 11, and the left and right sides of the material are cut off straight to define slant surfaces 19 that extend inwardly and gradually toward the lower side. In this embodiment, the slant surfaces 19 are formed in bilateral symmetry with each other so that the downward prolongations (as viewed in FIG. 1) of the slant surfaces 19 intersect each other.

Reference numeral 21 denotes a tubular member of the sheath 20 that is removably fitted over the insert part 10 from the distal end thereof. The tubular member 21 is formed in the shape of a thin-walled cylinder using a flexible and stretchable material, for example, silicone rubber.

A transparent distal end cover 22, made of a synthetic resin material, is connected to the distal end of the tubular member 21 in such a manner that no water will leak through the joint between the cover 22 and the tubular member 21. In use, the distal end cover 22 is removably fitted over the distal end part 13.

Figure 2:
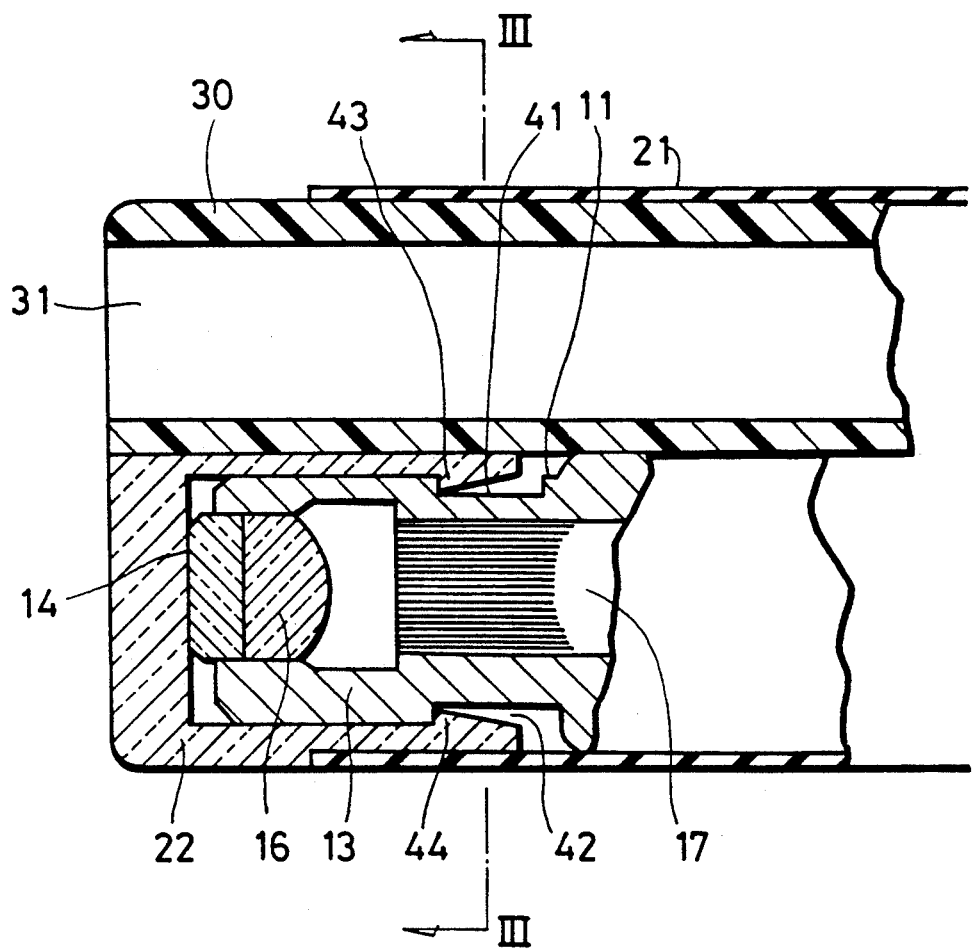
FIG. 2 is a sectional side view of the sheath according to the first embodiment, which is assembled to the insert part of the endoscope.
Figure 3A:
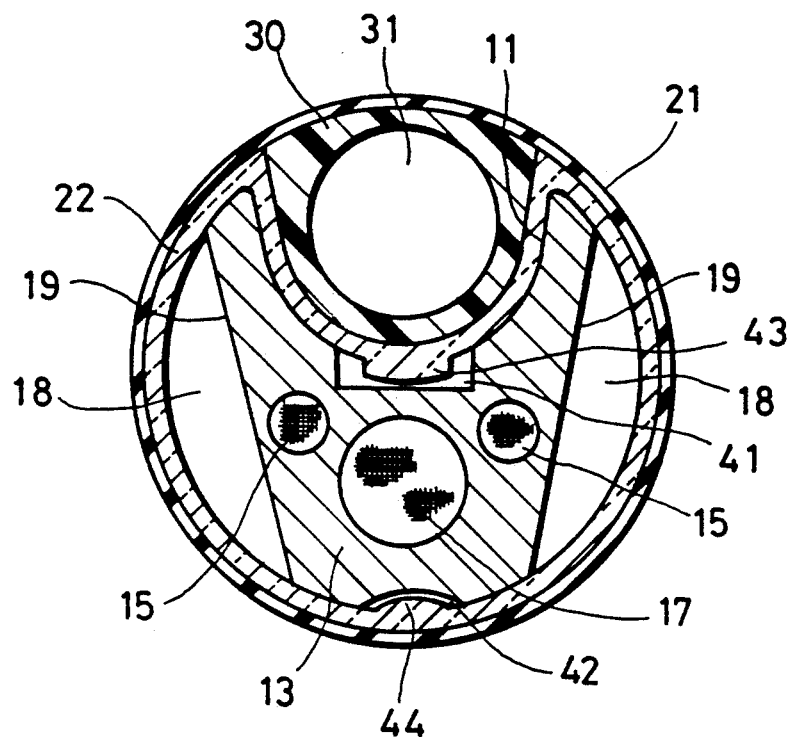
FIGS. 3A and 3B are sectional views taken along the line III—III in FIG. 2.

FIGS. 2 and 3A show the distal end portion of the sheath 20 which is attached to the insert part 10 of the endoscope. Reference numerals 16 and 17 denote an objective lens and an image guide fiber bundle, respectively, which are incorporated inside the viewing window 14 in the distal end part 13.

Since the distal end cover 22 of the sheath 20 has a cylindrical configuration, left and right spaces 18 are defined between the slant surfaces 19 of the distal end part 13 and the distal end cover 22.

Reference numeral 30 denotes a channel tube that defines a forceps inserting channel, which opens in the front face of the distal end cover 22.

The distal end of the channel tube 30 is rigidly secured to the distal end cover 22. The channel tube 30 extends through the tubular member 21 of the sheath 20 over the entire length thereof and is disposed in the U-shaped groove 11 in the insert part 10 of the endoscope.

Grooves 41 and 42 for click engagement are formed in the middle of the distal end part 13. The groove 41 is provided in the bottom of the U-shaped groove 11, and the groove 42 is provided in a portion of the lower end of the distal end part 13 which is substantially on a straight line that bisects the angle between the two slant surfaces 19. On the other hand, the rear end portion of the distal end cover 22 is provided with click pawls 43 and 44, which project inwardly so as to be engageable with the grooves 41 and 42, respectively.

Each of the click pawls 43 and 44 projects inwardly at right angles at the inner end portion thereof (the left-hand side as viewed in FIG. 2) and forms a surface that gently slants toward the rear end.

Accordingly, when the sheath 20 is to be attached to the insert part 10 of the endoscope, the distal end cover 22 of the sheath 20 is forced onto the distal end part 13 so as to cover the outer periphery of it. In consequence, the click pawls 43 and 44 are elastically deformed and hence temporarily expanded outwardly, and thereafter, the click pawls 43 and 44 engage the grooves 41 and 42, as shown in FIGS. 2 and 3A. As a result, the distal end cover 22 is locked to the distal end part 13 in a state where the spring action caused by of the elastic deformation of the distal end cover 22 acts on the engagement between the click pawls 43 and 44 and the grooves 41 and 42.

Thus, the tubular member 21 and the distal end cover 22 of the sheath 20 isolate the insert part 10 of the endoscope from the external environment, and the distal end face of the insert part 10, that is, the surfaces of the viewing window 14 and the illuminating windows 15, are kept in close contact with the inner surface of the distal end cover 22. In this state, since the click pawls 43 and 44 are engaged with the grooves 41 and 42, the sheath 20 cannot be removed from the insert part 10 of the endoscope.

Figure 3B:
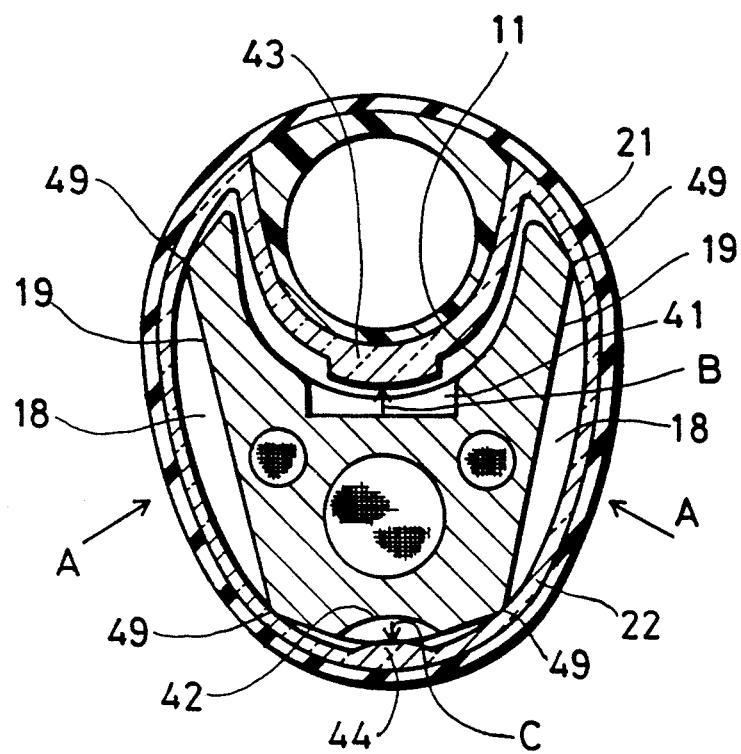

After the completion of an endoscopic inspection, the distal end cover 22 is pinched with fingertips from the left and right sides thereof toward the spaces 18, thereby elastically deforming the distal end cover 22 into a vertically elongated shape, as shown in FIG. 3B.

As a result, the click pawls 43 and 44 move in radially outward directions in which they disengage from the grooves 41 and 42, so that the engagement between these members can be canceled.

However, when the distal end cover 22 is merely elastically deformed into a vertically elongated shape, the distal end cover 22 may be deformed only at the lower portion since it is more deformable than the upper portion. In such a case, the click pawl 43 may not completely disengage from the groove 41 in the bottom of the U-shaped groove 11.

In this embodiment, however, the left and right side surfaces of the distal end part 13 are formed into slant surfaces that extend inwardly and gradually toward the lower side. For this reason, when the distal end cover 22 is pinched perpendicularly to the slant surfaces 19, as shown by the arrows A in FIG. 3B, force acts in a radially outward direction B about four fulcra 49 so as to raise the upper portion of the distal end cover 22 as well as in a radially outward direction C.

Accordingly, the engagement between the click pawl 43 and the groove 41 in the bottom of the U-shaped groove 11 can be canceled reliably. In addition, the engagement between the groove 42 and the click pawl 44 on the lower portion of the distal end cover 22, which is more deformable into an elongated shape, is simultaneously canceled.

Once the click pawls 43 and 44 are disengaged from the grooves 41 and 42 by pinching the distal end cover 22 from both sides thereof, the sheath 20 can be readily removed from the insert part 10 of the endoscope and replaced with a new one.

It should be noted that a click pawl may be provided only for one of the U-shaped grooves 41 and 42 and that the click pawls 43 and 44 are not necessarily formed as integral parts of the distal end cover 22, but may be provided as discrete parts. The distal end cover 22 need not be transparent throughout, but only at portions that face the observation and illuminating light paths.

According to the present invention, the distal end cover of the sheath can be readily and reliably secured to the distal end of the insert part of the endoscope without a gap therebetween and yet the sheath can be readily disengaged and removed from the insert part simply by pinching the distal end cover by fingertips.

Since the transparent portion of the distal end cover is brought into close contact with the distal end of the insert part when the cover is secured to the insert part, it is possible to perform favorable endoscopic observation without the appearance of a flare or ghost in the observation field of view.

FIG. 4, which is a perspective view of a second embodiment of the present invention, shows an insert part 110 of an endoscope and the distal end portion of a sheath 120 that is removably fitted over the insert part 110.

The insert part 110 as a whole is formed from an elongate flexible tube. The insert part 110 is formed with a U-shaped groove 111 that extends axially over the entire length thereof.

A bendable portion 112 that is bendable by remote control is formed at the distal end of the insert part 110. A distal end part 113 that incorporates an objective optical system for observation is connected to the distal end of the bendable portion 112. The distal end face of the distal end part 113 is provided with a viewing window 114 for the objective optical system and illuminating windows 115 where the emergent end of a light guide fiber bundle is disposed. The windows 114 and 115 slightly project to the same height from the distal end face of the distal end part 113. The endoscope of this embodiment is an end-viewing endoscope and therefore both of the optical axes of the observation light and the illuminating light are coincident with the axis of the insert part 110.

Reference numeral 121 denotes a tubular member of the sheath 120 that is removably fitted over the insert part 110 from the distal end thereof. The tubular member 121 is formed in the shape of a thin-walled cylinder using a flexible and stretchable material, for example, silicone rubber. A transparent distal end cover 122 is connected to the distal end of the tubular member 121 in such a manner that no water will leak through the joint between the cover 122 and the tubular member 121. In use, the distal end cover 122 is removably fitted over the distal end part 113. The distal end cover 122 is formed from a shape-memory synthetic resin material that is restored to a previously memorized shape by heating it to a given shape restoration temperature.

A shape-memory synthetic resin material is obtained by crosslinking certain synthetic resin materials. It is possible to employ, for example, polynorbornene that is formed by a ring-opening polymerization of norbornene that is synthesized by the Diels-Alder reaction from ethylene and cyclopentadiene. The shape restoration temperature can be set relatively arbitrarily, but in the application of the present invention it is preferable to set the shape restoration temperature at about 50° to 60° C.

In production, the distal end cover 122 is first formed by crosslinking into a memorized shape to which the distal end cover 122 is to be restored upon heating (the memorized shape will be explained later). Next, the distal end cover 122 is made amorphous by heating it to a temperature above the melting point and is then deformed into a shape for actual use, shown in FIGS. 4 to 6, and crystallized by cooling. Thus, the deformed state is fixed.

When the distal end cover 122 in the deformed state is heated to the shape restoration temperature, it is restored to the original shape (memorized shape), and this shape is maintained even when the temperature lowers.

Figure 5:
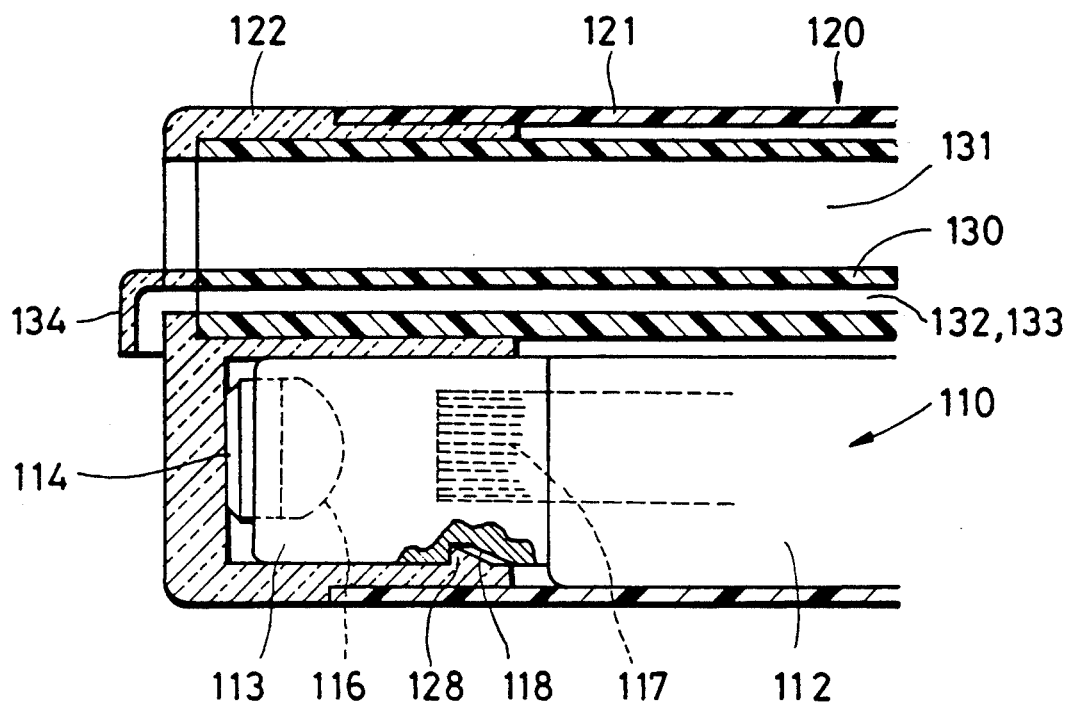
FIG. 5 is a sectional side view of the sheath according to the second embodiment, which is assembled to the insert part of the endoscope.
Figure 6:
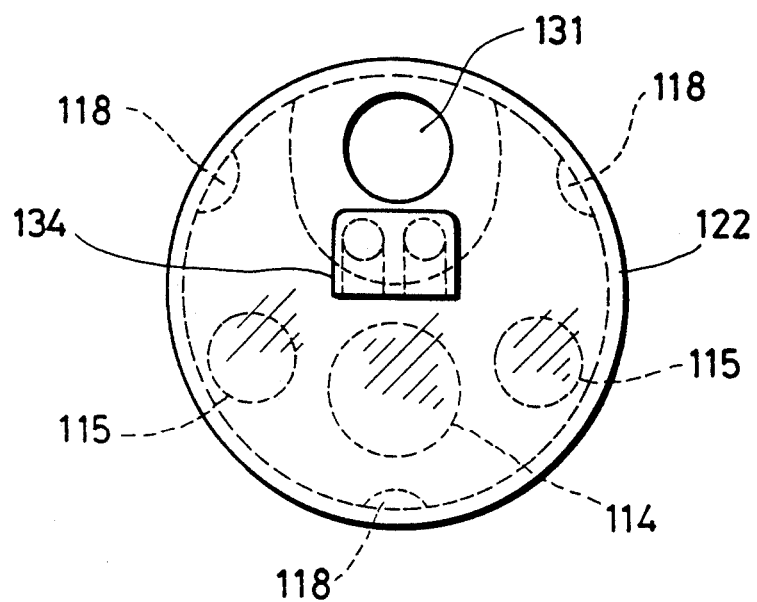
FIG. 6 is a front view of the sheath according to the second embodiment, which is assembled to the insert part of the endoscope.

FIGS. 5 and 6 show the distal end portion of the sheath 120 which is attached to the insert part 110 of the endoscope. Reference numerals 116 and 117 denote an objective lens and an image guide fiber bundle, respectively, which are incorporated inside the viewing window 114 in the distal end part 113.

Reference numeral 130 denotes a channel tube that is formed with a forceps inserting channel 131 and air and water supply channels 132 and 133, which open in the front face of the distal end cover 122. The distal end of the channel tube 130 is rigidly secured to the distal end cover 122. The channel tube 130 extends through the tubular member 121 of the sheath 120 over the entire length thereof and is disposed in the U-shaped groove 111 in the insert part 110 of the endoscope. A nozzle 134 is provided to direct the outlets of the air and water supply channels 132 and 133 toward the surface of the distal end cover 122 in front of the viewing window 114.

The outer peripheral surface of the distal end part 113 of the endoscope is formed with, for example, three recesses 118 at respective positions. On the other hand, the inner peripheral surface of the distal end cover 122 of the sheath 120 is integrally formed with projections 128 which are engageable with the recesses 118 in the outer peripheral surface of the distal end part 113.

As shown in FIG. 5, each projection 128 projects inwardly at right angles at the inner end portion thereof (the left-hand side as viewed in FIG. 5) and forms a surface that gently slants toward the rear end.

Figure 7:
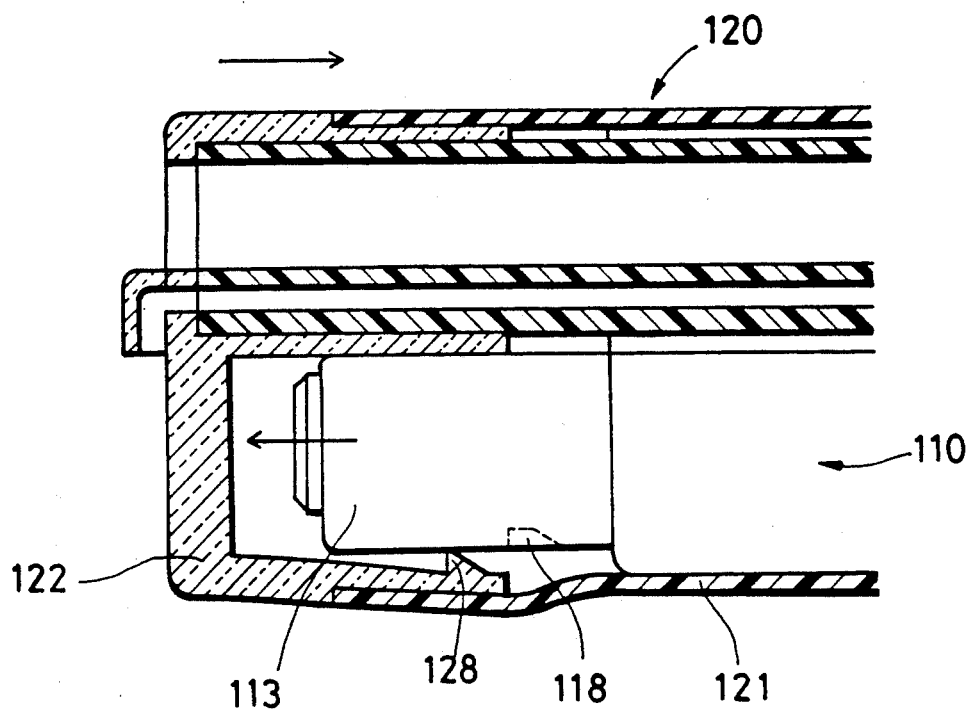
FIG. 7 is a sectional side view of the sheath according to the second embodiment, which is being attached to the insert part of the endoscope.

Accordingly, when the sheath 120 is to be attached to the insert part 110 of the endoscope, the distal end cover 122 of the sheath 120 is forced onto the distal end part 113 so as to cover the outer periphery of it (see FIG. 7). In consequence, the projections 128 are elastically deformed and hence temporarily expanded outwardly, and thereafter, the projections 128 engage the recesses 118, as shown in FIG. 5. As a result, the distal end cover 122 is locked to the distal end part 113 in a state where the spring action caused by the elastic deformation of the distal end cover 122 acts on the engagement between the projections 128 and the recesses 118.

In the state that is shown in FIG. 5, the tubular member 121 and the distal end cover 122 of the sheath 120 isolate the insert part 110 of the endoscope from the external environment, and the viewing window 114 and the illuminating windows 115 are kept in close contact with the inner surface of the distal end cover 122. At ordinary temperatures, the distal end cover 122 maintains the state that is shown in FIG. 5 and hence the projections 128 cannot disengage from the recesses 118, so that the above-described state is maintained.

However, since the distal end cover 122 is formed from a shape-memory synthetic resin material, as stated above, it can be restored to the original shape (memorized shape) by heating it to a temperature above the shape restoration temperature with hot water or hot air after the completion of an endoscopic inspection.

Figure 8A:
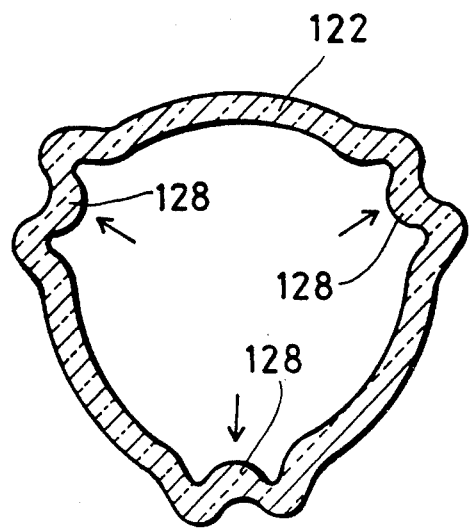
FIGS. 8A and 8B are sectional front views of a distal end cover in the second embodiment of the present invention.
Figure 8B:
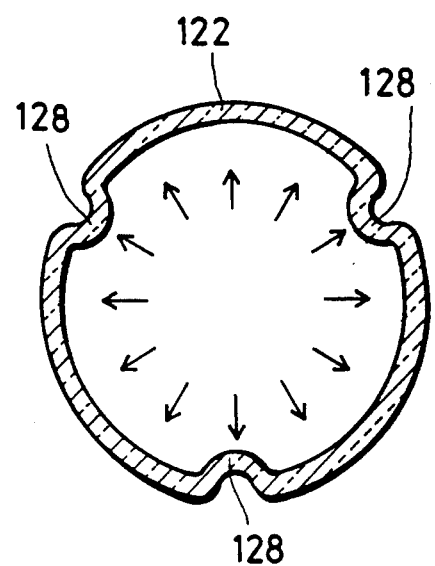
Figure 9:
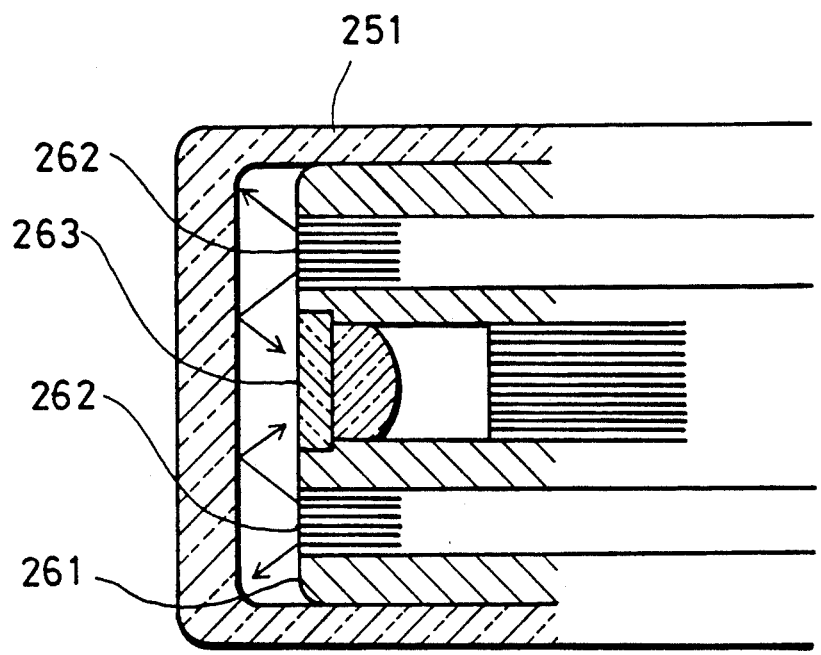
FIG. 9 is a sectional side view of a sheath according to a prior art, which is assembled to an insert part of an endoscope.

There is no particular restriction on the original (memorized) shape of the distal end cover 122. It is possible to employ any shape that allows the projections 128 to disengage from the recesses 118, for example, a shape in which only those portions where the projections 128 are located project outwardly, as shown in FIG. 8A, or a shape in which the whole distal end cover 122 has a greater diameter than that of the deformed shape, as shown in FIG. 8B.

Once the projections 128 are disengaged from the recesses 118 by heating the distal end cover 122, the sheath 120 can be readily removed from the insert part 110 of the endoscope and replaced with a new one.

It should be noted that the projections 128 are not necessarily formed as integral parts of the distal end cover 122, but may be provided as discrete parts. The distal end cover 122 need not be transparent throughout, but only at portions that face the observation and illuminating light paths.

According to the present invention, the distal end cover of the sheath can be readily and reliably secured to the distal end of the insert part of the endoscope so that the distal end cover will not be displaced, and yet the sheath can be readily disengaged and removed from the insert part simply by heating the distal end cover.

Since the transparent portion of the distal end cover is brought into close contact with the distal end of the insert part when the cover is secured to the insert part, it is possible to perform favorable endoscopic observations without the appearance of a flare or ghost in the observation field of view.

While the invention has been described by reference to specific embodiments chosen for purposes of illustration, it should be apparent that numerous modifications could be made thereto by those skilled in the art without departing from the basic concept and scope of the invention.

I claim:

1. A sheathed endoscope having a flexible elongate insert part and a sheath that is removably fitted over said insert part, comprising:
    a distal end part that is provided at the distal end of said insert part;
    a distal end cover that is provided at the distal end of said sheath and that is removable fitted over said distal end part;
    lock means that is provided on said distal end cover so as to be engageable with said distal end part, said lock means being disengaged from said distal end part by deforming said distal end cover so that said lock means moves radially outward; and
    wherein a space is defined between said distal end cover and a side surface of said distal end part, and said lock means is disengaged from said distal end part by elastically deforming said distal end cover inwardly toward said space from the outside.

2. A sheathed endoscope according to claim 1, wherein said lock means is a click pawl that projects inwardly from said distal end cover.

3. A sheathed endoscope according to claim 1, wherein said distal end cover is transparent at least a portion thereof that faces an optical path of said endoscope, said transparent portion of said distal end cover being brought into close contact with the distal end face of said insert part when said lock means is engaged with said distal end part.

4. A sheathed endoscope according to claim 1, wherein the distal end of a channel tube for inserting a tool for an endoscopic procedure is attached to said distal end cover; the outer surface of said distal end part is formed with a U-shaped groove for avoiding interference with said channel tube; and an engagement portion that is engageable with said lock means is formed in the bottom of said U-shaped groove.

5. A sheathed endoscope according to claim 1, comprising spaces being defined between said distal end cover and two side surfaces of said distal end part, and said lock means is disengaged from said distal end part by elastically deforming said distal end cover inwardly toward said spaces from the outside.

6. A sheathed endoscope according to claim 5, wherein said distal end part has straight side surfaces at two sides thereof which are in opposed relationship with respect to each other, so that said spaces are defined between said side surfaces of said distal end part and the inner surface of said distal end cover.

7. A sheathed endoscope according to claim 5, wherein said two side surfaces of said distal end part are slant surfaces, the prolongations of which intersect each other at one side thereof, and said lock means being provided substantially on a straight line that bisects the angle between said two slant surfaces.

8. A sheathed endoscope according to claim 1, including at least two spaces being defined between said distal end cover and at least two side surfaces of said distal end part.

9. A sheathed endoscope having a flexible elongate insert part and a sheath that is removably fitted over said insert part, comprising:
    a distal end part that is provided at the distal end of said insert part;
    a distal end cover that is provided at the distal end of said sheath and that is removably fitted over said distal end part;
    lock means that is provided on said distal end cover so as to be engageable with said distal end part, said lock means being disengaged from said distal end part by deforming said distal end cover so that said lock means moves radially outward;
    spaces being defined between said distal end cover and two side surfaces of said distal end part, said lock means being disengaged from said distal end part by elastically deforming said distal end cover inwardly toward said spaces from the outside; and
    said two side surfaces of said distal end part being slant surfaces, the prolongations of which intersect each other at one side thereof, and said lock means being provided substantially on a straight line that bisects the angle between said two slant surfaces.

* * * * *

UNITED STATES PATENT AND TRADEMARK OFFICE
CERTIFICATE OF CORRECTION

PATENT NO. : 5,257,617
DATED : November 2, 1993
INVENTOR(S) : Nagashige TAKAHASHI It is certified that error appears in the above-indentified patent and that said Letters Patent is hereby corrected as shown below:

At column 7, line 53 (claim 1, line 7) change "removable" to ---removably---.

At column 8, line 5 (claim 3, line 2) change "transparent at least" to ---transparent at at least---.

Signed and Sealed this

Twenty-ninth Day of August, 1995

Attest:

BRUCE LEHMAN

*Attesting Officer*          *Commissioner of Patents and Trademarks*